(12) United States Patent
Song et al.

(10) Patent No.: US 11,382,605 B2
(45) Date of Patent: Jul. 12, 2022

(54) ULTRASOUND PROBE, ULTRASOUND IMAGING APPARATUS AND METHOD OF CONTROLLING THE ULTRASOUND IMAGING APPARATUS

(71) Applicant: SAMSUNG ELECTRONICS CO., LTD., Suwon-si (KR)

(72) Inventors: Jong Keun Song, Yongin-si (KR); Tae Ho Jeon, Seoul (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 739 days.

(21) Appl. No.: 15/867,945

(22) Filed: Jan. 11, 2018

(65) Prior Publication Data
US 2018/0192999 A1    Jul. 12, 2018

(30) Foreign Application Priority Data

Jan. 12, 2017    (KR) ........................ 10-2017-0005262

(51) Int. Cl.
*A61B 8/00*    (2006.01)
*A61B 8/14*    (2006.01)
*A61B 8/08*    (2006.01)

(52) U.S. Cl.
CPC ................ *A61B 8/54* (2013.01); *A61B 8/145* (2013.01); *A61B 8/4405* (2013.01);
(Continued)

(58) Field of Classification Search
None
See application file for complete search history.

(56) References Cited

U.S. PATENT DOCUMENTS 7,439,656 B2    10/2008    Ossmann
8,628,474 B2    1/2014    Chiang et al.
(Continued)

FOREIGN PATENT DOCUMENTS

CN             1189217 A       7/1998
KR    10-2012-0121230 A      11/2012
(Continued)

OTHER PUBLICATIONS

Communication dated Sep. 5, 2018 issued by the Korean Intellectual Property Office in counterpart Korean Application No. 10-2017-0005262.

(Continued)

*Primary Examiner* — Katherine L Fernandez
(74) *Attorney, Agent, or Firm* — Sughrue Mion, PLLC

(57) ABSTRACT

An ultrasound probe, including a transducer module configured to receive an echo ultrasound signal reflected from a subject in response to a transmitted ultrasound signal, and a driver chip provided in the transducer module, the driver chip being configured to focus at least one of the ultrasound signal and the echo ultrasound signal, wherein the driver chip includes a fine analog beamformer configured to apply a fine delay and a coarse analog beamformer configured to apply a coarse delay, wherein the fine analog beamformer is arranged in a first inner region of a plurality of inner regions of the driver chip, the first inner region being located opposite to the transducer module, and wherein the coarse analog beamformer is arranged in a second inner region of the plurality of inner regions of the driver chip, the second inner region being different from the first inner region.

13 Claims, 19 Drawing Sheets

(52) U.S. Cl.
CPC ............ *A61B 8/4488* (2013.01); *A61B 8/483* (2013.01); *A61B 8/4444* (2013.01); *A61B 8/4494* (2013.01)

(56) References Cited

U.S. PATENT DOCUMENTS

| | | | |
|---|---|---|---|
| 2008/0294046 A1* | 11/2008 | Chiang | G01S 7/5208 |
| | | | 600/447 |
| 2012/0179044 A1* | 7/2012 | Chiang | A61B 8/145 |
| | | | 600/447 |
| 2013/0226001 A1 | 8/2013 | Steen et al. | |
| 2016/0019881 A1* | 1/2016 | Kim | G10K 11/346 |
| | | | 367/7 |

FOREIGN PATENT DOCUMENTS

| | | |
|---|---|---|
| KR | 10-2013-0068529 A | 6/2013 |
| KR | 10-2016-0101140 A | 8/2016 |

OTHER PUBLICATIONS

Communication issued by the Korean Intellectual Property Office dated Jan. 17, 2018 in counterpart Korean Patent Application No. 10-2017-0005262.

Communication dated Jun. 18, 2020 by the State Intellectual Property Office of P.R. China in counterpart Chinese Patent Application No. 201810031091.3.

Communication dated Mar. 5, 2021 issued by the State Intellectual Property Office of the P.R.China in application No. 201810031091.3.

* cited by examiner

ULTRASOUND PROBE, ULTRASOUND IMAGING APPARATUS AND METHOD OF CONTROLLING THE ULTRASOUND IMAGING APPARATUS

CROSS-REFERENCE TO RELATED APPLICATION

This application claims the benefit of Korean Patent Application No. 10-2017-0005262, filed on Jan. 12, 2017 in the Korean Intellectual Property Office, the disclosure of which is incorporated herein by reference in its entirety.

BACKGROUND

1. Field

Exemplary embodiments of the present disclosure relate to an ultrasound probe configured to generate an ultrasound image, an ultrasound imaging apparatus, and a method of controlling the ultrasound imaging apparatus.

2. Description of Related Art

An ultrasound imaging apparatus may be an apparatus which emits an ultrasound signal toward a target part in a body of a subject from a surface of the subject, and noninvasively obtains a tomographic image of soft tissue of the subject or an image of a blood flow using information of an ultrasound signal, for example an ultrasound echo signal, reflected from the target part.

The ultrasound imaging apparatus may have a small size, may be relatively inexpensive, may be capable of displaying an image in real time, may cause no radiation exposure, and thus may be very safe, compared to other medical imaging apparatuses such as an X-ray imaging apparatus, an X-ray computerized tomography (CT) scanner, a magnetic resonance imaging (MRI) apparatus, a nuclear medicine imaging apparatus, etc. Thus, the ultrasound imaging apparatus has been widely used for diagnosis in the fields of a cardiology, gastroenterology, urology, obstetrics and gynecology.

The ultrasound imaging apparatus may include an ultrasound probe to transmit or receive an ultrasound wave. The ultrasound probe may transmit an ultrasound wave to a subject via a transducer and receive an echo ultrasound wave reflected from the subject.

SUMMARY

Therefore, it is an aspect of the present disclosure to provide an ultrasound probe capable of performing two-step analog beamforming.

Additional aspects of the disclosure will be set forth in part in the description which follows and, in part, will be obvious from the description, or may be learned by practice of the disclosure.

According to an aspect of an exemplary embodiment, an ultrasound probe includes a transducer module configured to receive an echo ultrasound signal reflected from a subject in response to a transmitted ultrasound signal, and a driver chip provided in the transducer module, the driver chip being configured to focus at least one of the ultrasound signal and the echo ultrasound signal, wherein the driver chip includes a fine analog beamformer configured to apply a fine delay and a coarse analog beamformer configured to apply a coarse delay, wherein the fine analog beamformer is arranged in a first inner region of a plurality of inner regions of the driver chip, the first inner region being located opposite to the transducer module, and wherein the coarse analog beamformer is arranged in a second inner region of the plurality of inner regions of the driver chip, the second inner region being different from the first inner region.

The driver chip may include an application-specific integrated circuit (ASIC).

The ultrasound probe may further include a plurality of coarse analog beamformers are configured to apply the coarse delay to a plurality of subgroups of a transducer array included in the transducer module.

A number of the plurality of subgroups may be determined according to channel information of an ultrasound image and a number of transducer elements of the transducer module.

The ultrasound may further include a circuit board at a bottom of the driver chip, the circuit board including a probe controller configured to control the fine analog beamformer and the coarse analog beamformer.

The driver chip may be electronically connected to the circuit board.

The probe controller may be further configured to control the coarse analog beamformer to input a signal to which the coarse delay is applied to the fine analog beamformer, and to control the fine analog beamformer to transmit an ultrasound signal based on an output signal to which the fine delay is applied.

When an echo ultrasound signal is received through the transducer module, the probe controller may be further configured to control the fine analog beamformer to output a signal obtained by applying the fine delay to the echo ultrasound signal, and to control the coarse analog beamformer to output an echo signal by applying the coarse delay to the output signal.

The fine analog beamformer may be provided for each transducer element included in the plurality of subgroups, and the coarse analog beamformer may be provided for each subgroup of the plurality of subgroups.

According to an aspect of an exemplary embodiment, an ultrasound imaging apparatus includes an ultrasound probe including a transducer module configured to receive an echo ultrasound signal reflected from a subject, in response to a transmitted ultrasound signal, and a driver chip provided in the transducer module, the driver chip being configured to focus at least one of the ultrasound signal and the echo ultrasound signal, wherein the driver chip includes a fine analog beamformer configured to apply a fine delay, and a coarse analog beamformer configured to apply a coarse delay, and a main controller configured to control an ultrasound image generated based on the echo ultrasound signal to be displayed on a display, wherein the fine analog beamformer is arranged in a first inner region of a plurality of inner regions of the driver chip, the first inner region being located opposite to the transducer module, and wherein the coarse analog beamformer is arranged in a second inner region of the plurality of inner regions of the driver chip, the second inner region being different from the first inner region.

The ultrasound imaging apparatus may further include a plurality of coarse analog beamformers configured to apply the coarse delay to a plurality of subgroups of a transducer array included in the transducer module.

A number of the plurality of subgroups may be determined according to channel information of an ultrasound image and a number of transducer elements of the transducer module.

The ultrasound imaging apparatus may further include a circuit board at a bottom of the driver chip, the circuit board including a probe controller configured to control the fine analog beamformer and the coarse analog beamformer.

The probe controller may be further configured to control the coarse analog beamformer to input a signal to which the coarse delay is applied to the fine analog beamformer, and to control the fine analog beamformer to transmit an ultrasound signal based on an output signal to which the fine delay is applied.

When an echo ultrasound signal is received through the transducer module, the probe controller may be further configured to control the fine analog beamformer to output a signal obtained by applying the fine delay to the echo ultrasound signal, and to control the coarse analog beamformer to output an echo signal by applying the coarse delay to the output signal.

The fine analog beamformer may be provided for each transducer element included in the plurality of subgroups, and the coarse analog beamformer may be provided for each subgroup of the plurality of subgroups.

According to an aspect of an exemplary embodiment, a method of controlling an ultrasound imaging apparatus includes receiving an echo ultrasound signal in response to a transmitted ultrasound signal, outputting an echo signal by applying a fine delay and a coarse delay to the echo ultrasound signal using a fine analog beamformer and a coarse analog beamformer, and displaying on a display an ultrasound image reconstructed based on of the echo signal, wherein the fine analog beamformer and the coarse analog beamformer are included in one driver chip provided in an ultrasound probe.

BRIEF DESCRIPTION OF THE DRAWINGS

These and/or other aspects of the disclosure will become apparent and more readily appreciated from the following description of the exemplary embodiments, taken in conjunction with the accompanying drawings of which.

DETAILED DESCRIPTION

Figure 1:
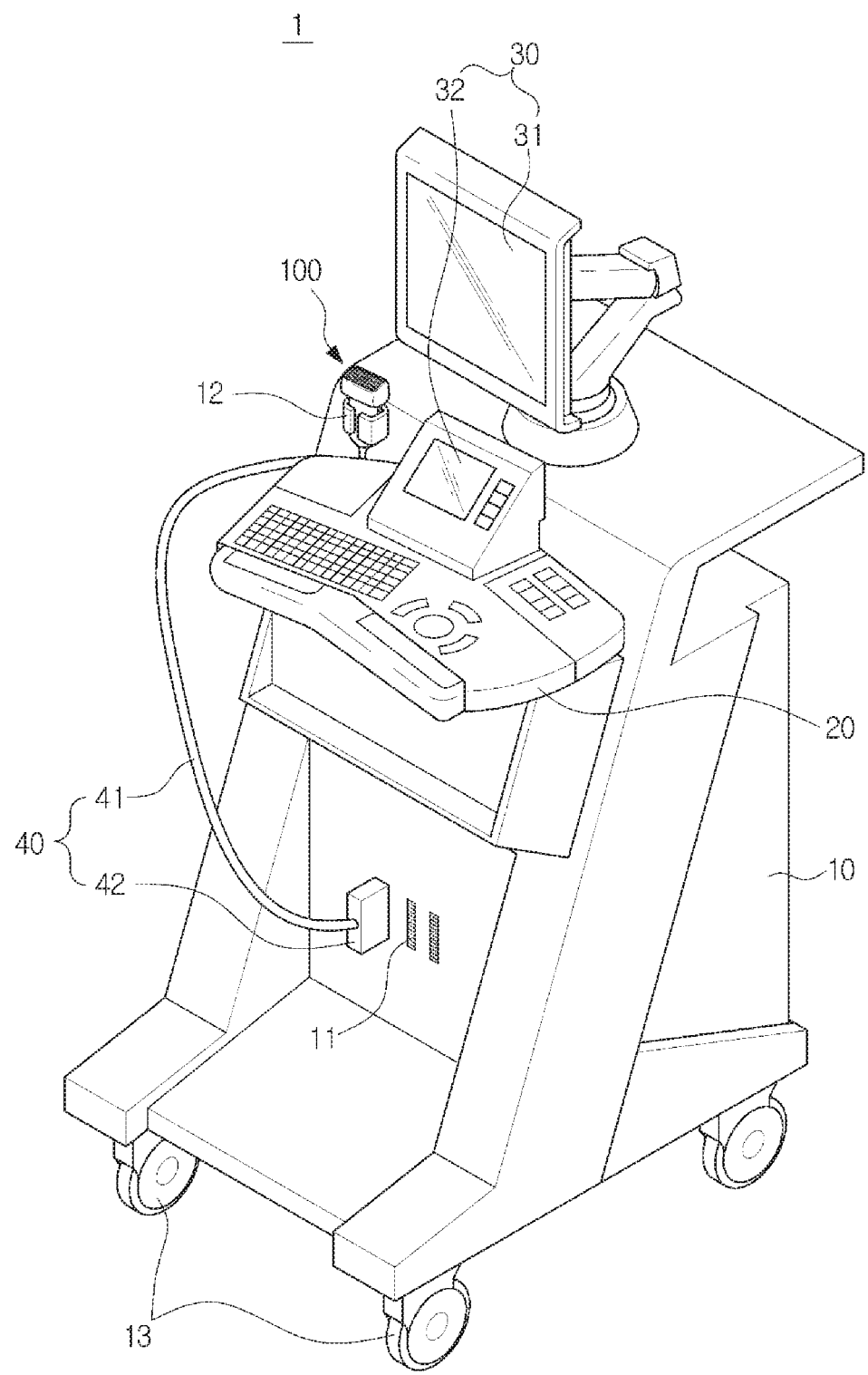
FIG. 1 is a diagram illustrating an ultrasound imaging apparatus in accordance with an exemplary embodiment.

Reference will now be made in detail to the exemplary embodiments of the present disclosure, examples of which are illustrated in the accompanying drawings, wherein like reference numerals refer to like elements throughout.

FIG. 1 is a diagram illustrating an ultrasound imaging apparatus in accordance with an exemplary embodiment.

Referring to FIG. 1, an ultrasound imaging apparatus 1 in accordance with an exemplary embodiment of the present disclosure may include a main body 10, an input device 20, a display 30, and an ultrasound probe 100.

At least one connection part 11 may be provided in a side of a main body 10. A connector 42 connected to a cable 41 may be physically coupled to the at least one connection part 11.

The main body 10 may include a holder 12 for holding the ultrasound probe 100. A tester may store the ultrasound probe 100 by holding the ultrasound probe 100 with the holder 12 when the ultrasound imaging apparatus 1 is not in use.

The main body 10 may include a moving device 13 at a bottom thereof to move the ultrasound imaging apparatus 1. The moving device 13 may be a plurality of casters provided at a bottom surface of the main body 10. The plurality of casters may be aligned to move the main body 10 in a specific direction or may be provided to be freely movable so as to move the ultrasound imaging apparatus 1 in a desired direction. The moving device 13 may include a locking device such that the moving device 13 may be stopped at a desired location. The ultrasound imaging apparatus 1 described above is referred to as a cart type ultrasound imaging apparatus.

A form of the main body 10 of the ultrasound imaging apparatus 1 is not limited to that illustrated in FIG. 1. For example, the main body 10 of the ultrasound imaging apparatus 1 may be embodied as a smart phone, as well as a laptop computer, a desk top computer, or a tablet personal computer (PC). As another example, the ultrasound imaging apparatus 1 may be embodied as a mobile terminal such as a personal digital assistant (PDA), a watch detachable from a user's body, or a glasses type wearable terminal, and a form thereof is not limited.

An example of a form of the main body 10 will be described with reference to FIG. 1 below but exemplary embodiments which will be described below are not limited thereto. A display panel may be provided to visually display various images to a user and to perform various operations, and exemplary embodiments which will be described below are applicable to any device connectable to the ultrasound probe 100 via a communication network regardless of a form of the device.

The ultrasound probe 100 may be in contact with a surface of a subject to transmit or receive an ultrasound signal. In detail, the ultrasound probe 100 may transmit an ultrasound signal to a specific part inside a subject according to a transmission signal received from the main body 10, and receive an echo ultrasound signal reflected from the specific part inside the subject and transmit the echo ultrasound signal to the main body 10. Here, the echo ultrasound signal may be an ultrasound signal which is a radio-frequency (RF) signal reflected from the subject but is not limited thereto and may be understood to include all signals obtained by reflecting an ultrasound signal transmitted to the subject.

The subject may be a body of a human being or an animal but is not limited thereto provided that an image of an inner structure thereof may be obtained according to an ultrasound signal.

The ultrasound probe 100 may be coupled to the main body 10 via a connection member 40. The connection member 40 may include the cable 41 and the connector 42. An ultrasound probe 100 may be provided at one side of the cable 41 and the connector 42 may be provided at another side thereof. The connector 42 may be mounted to be separable from the connection part 11 of the main body 10. Accordingly, the ultrasound probe 100 may be coupled to the main body 10.

The ultrasound probe 100 may be coupled to the main body 10 through the connection member 40, and receive various signals for controlling the ultrasound probe 100 or transmit an analog signal or a digital signal corresponding to an echo ultrasound signal received by the ultrasound probe 100 via a wired communication network.

In detail, the wired communication network refers to a communication network through which a signal is exchanged via a wire. In one exemplary embodiment, the main body 10 may exchange various signals with the ultrasound probe 100 via a wired communication network such as a Peripheral Component Interconnect (PCI), PCI-express, or a Universal Serial Bus (USB) but is not limited thereto.

However, the ultrasound probe 100 is not limited thereto and may be connected to the main body 10 via a wireless communication network to receive various signals for controlling the ultrasound probe 100 or to transmit an analog signal or a digital signal corresponding to an echo ultrasound signal received by the ultrasound probe 100.

The wireless communication network refers to a communication network through which signals may be exchanged wirelessly. In this case, the main body 10 may establish wireless communication with the ultrasound probe 100 through at least one of a short-range communication module and a mobile communication module.

The short-range communication module refers to a module for short-range communication within a predetermined distance or less. Examples of short-range communication technology may include, but are not limited to, a wireless local area network (LAN), Wi-Fi, Bluetooth, ZigBee, Wi-Fi-Direct (WFD), an Infrared Data Association (IrDA) protocol, Bluetooth Low Energy (BLE), Near-Field Communication (NFC), etc.

The mobile communication module may transmit a radio signal to or receive a radio signal from at least one among a base station, an external terminal, and a server in the mobile communication network. Here, the radio signal may be understood to include various types of data. That is, the main body 10 may exchange signals including various types of data with the ultrasound probe 100 via at least one of a base station and a server.

However, wireless communication networks are not limited to examples described above and include all communication networks supporting exchange of radio signals between the ultrasound probe 100 and the main body 10.

For example, the main body 10 may exchange signals including various types of data with the ultrasound probe 100 via a base station in a mobile communication network such as 3G or 4G. In addition, the main body 10 may exchange data with either a hospital server connected to or other medical devices installed in a hospital and connected to a Picture Archiving and Communication System (PACS). Furthermore, the main body 10 may exchange data according to Digital Imaging and Communication in Medicine (DICOM) standards but is not limited thereto.

For convenience of explanation, a wired communication method and a wireless communication method will be hereinafter referred to collectively as a communication method when it is unnecessary to distinguish them individually, and a wired communication network and a wireless communication network will be hereinafter referred to collectively as a communication network when it is unnecessary to distinguish them individually.

A main controller 90 may be included in the main body 10 to control the overall operation of the ultrasound imaging apparatus 1, as well as an image processing process of converting an echo ultrasound wave received by the ultrasound probe 100 into an ultrasound image, as will be described in detail below.

The main body 10 may further include the input device 20. The input device 20 may be in the form of a keyboard, a foot switch, or a foot pedal. When the input device 20 is a keyboard, the keyboard may be provided on a top of the main body 10. The keyboard may include at least one among a switch, a key, a joystick, and a trackball. When the input device 20 is a foot switch or a foot pedal, the foot switch or the foot pedal may be provided at a bottom of the main body 10.

In addition, the input device 20 may be embodied as software, e.g., in the form of a graphical user interface. In this case, the input device 20 may be displayed on the display 30.

A tester may control the operation of the ultrasound imaging apparatus 1 via the input device 20. For example, a command instructing to select an A mode, a B mode, an M mode, or a Doppler image mode may be received via the input device 20. Furthermore, a command instructing to start an ultrasound diagnosis may be received via the input device 20. A command received via the input device 20 may be transmitted to the main body 10 through wired communication or wireless communication.

The display 30 may include a first display 31 and a second display 32. The display 30 may display an ultrasound image obtained during an ultrasound diagnosis process. Furthermore, the display 30 may display an application related to an operation of the ultrasound imaging apparatus 1. For example, the first display 31 may display an ultrasound image obtained during an ultrasound diagnosis process and the second display 32 may display details related to the operation of the ultrasound imaging apparatus 1.

The first display 31 and/or the second display 32 may include, but is/are not limited to, a cathode ray tube (CRT) display panel, a liquid crystal display (LCD) panel, a light-emitting diode (LED) panel, an organic light-emitting diode (OLED), a plasma display panel (PDP), or a field emission display (FED) panel.

The first display 31 and/or the second display 32 may be coupled to the main body 10 or separated from the main body 10 but is not limited thereto. Although FIG. 1 illustrates that the display 30 includes the first display 31 and the second display 32, the first display 31 or the second display 32 may be omitted in some cases.

When the first display 31 and/or the second display 32 is/are embodied as a touch type display, the first display 31 and/or the second display 32 may also perform a function of the input device 20. That is, a user may input various commands via the display 30 or the input device 20.

A structure of the ultrasound probe 100 will be described in more detail below.

Figure 2:
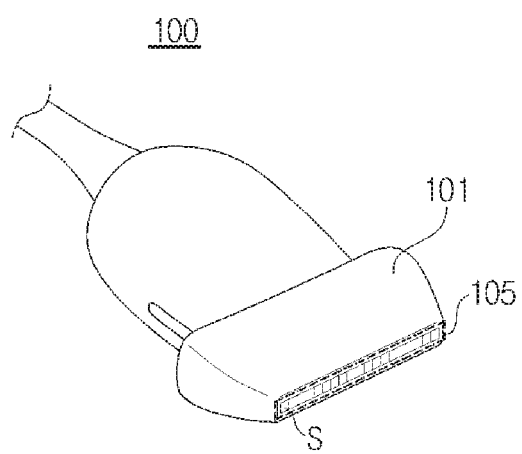
FIG. 2 is a diagram schematically illustrating the appearance of an ultrasound probe having a one-dimensional (1D) transducer array, in accordance with an exemplary embodiment.
Figure 3:
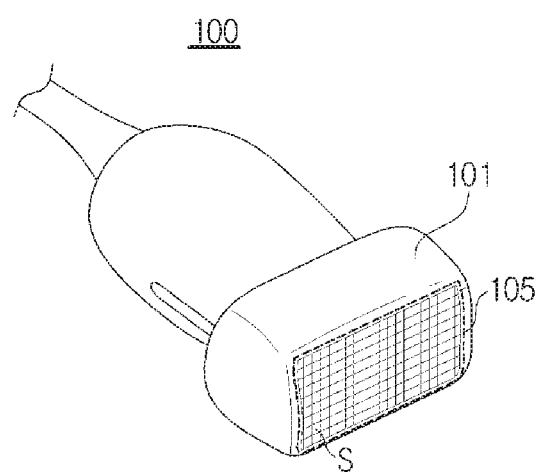
FIG. 3 is a diagram schematically illustrating the appearance of an ultrasound probe having a two-dimensional (2D) transducer array, in accordance with an exemplary embodiment.

FIG. 2 is a diagram schematically illustrating the appearance of an ultrasound probe having a one-dimensional (1D) transducer array, in accordance with an exemplary embodiment. FIG. 3 is a diagram schematically illustrating the appearance of an ultrasound probe having a two-dimensional (2D) transducer array, in accordance with an exemplary embodiment. FIGS. 2 and 3 will be described together below to avoid redundancy.

An ultrasound probe 100 is configured to be in contact with a surface of a subject and may emit an ultrasound signal. In detail, the ultrasound probe 100 may emit an ultrasound signal into a subject, and receive an echo ultrasound signal reflected from a specific inner part of the subject and transmit the echo ultrasound signal to the ultrasound imaging apparatus 1, according to a control command signal received from the main body 10 of the ultrasound imaging apparatus 1 of FIG. 1. Thus, the ultrasound probe 100 may transmit the echo ultrasound signal received from the subject to the main body 10 of the ultrasound imaging apparatus 1 via a communication network.

Alternatively, the ultrasound probe 100 may obtain an ultrasound image from an echo ultrasound signal and transmit the ultrasound image to the main body 10 of the ultrasound imaging apparatus 1 via the communication network. Alternatively, the ultrasound probe 100 may transmit data, which is obtained by performing some of various image processing processes required to obtain an ultrasound image from an echo ultrasound signal, to the main body 10 of the ultrasound imaging apparatus 1. However, exemplary embodiments are not limited thereto.

Referring to FIGS. 2 and 3, the ultrasound probe 100 may include a case 101, and a transducer array 105 provided at an inner side of the case 101.

A part of the transducer array 105 may be exposed to the outside of the case 101 via an opening formed in a front side of the case 101. Thus, the ultrasound probe 100 may transmit or receive an ultrasound signal while being in contact with a surface of a subject.

In this case, the transducer array 105 may convert an electrical signal into an ultrasound signal or convert an ultrasound signal into an electrical signal to transmit an ultrasound wave into the subject. The transducer array 105 may include a plurality of transducer elements S.

The transducer array 105 may be embodied in various forms. For example, the transducer array 105 may be a 1D transducer array as illustrated in FIG. 2. As another example, the transducer array 105 may be a 2D transducer array as illustrated in FIG. 3.

The ultrasound probe 100 including the transducer array 105 which is a 2D transducer array will be described below for convenience of explanation but exemplary embodiments which will be described below are not limited thereto.

For example, each of the transducer elements S of the transducer array 105 may convert an ultrasound signal into an electrical signal or convert an electrical signal into an ultrasound signal. To this end, each of the transducer elements S may be embodied as a magnetostrictive ultrasound transducer using a magnetostrictive effect of a magnetic substance, a piezoelectric ultrasound transducer using a piezoelectric effect of a piezoelectric material, a piezoelectric micromachined ultrasound transducer (pMUT), or the like. Otherwise, each of the transducer elements S may be embodied as a capacitive micromachined ultrasound transducer (cMUT) transmitting or receiving an ultrasound wave using the vibration of several hundreds or several thousands of micromachined thin films.

The transducer array 105 may be arranged in a linear form or a convex shape. The basic operating principle of the ultrasound probe 100 is the same regardless of whether the transducer array 105 is arranged in the linear form or the convex shape. However, an ultrasound image generated by the ultrasound probe 100 including the transducer array 105 arranged in the convex shape may be in a fan shape because an ultrasound wave emitted from transducer array 105 is in a fan shape. Although a case in which the transducer array 105 is arranged in the linear form will be described below for convenience of explanation, exemplary embodiments which will be described below are not limited thereto.

Figure 4:
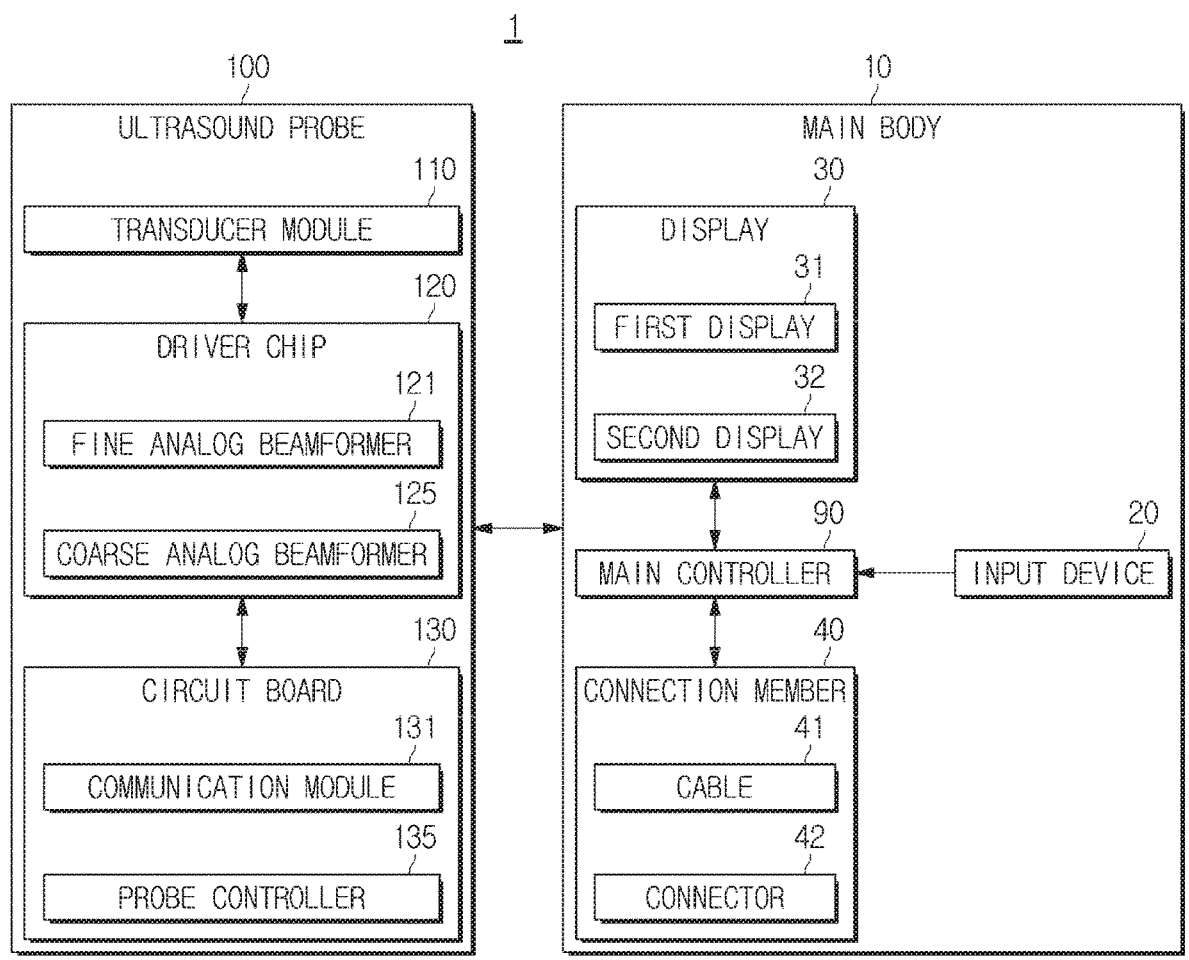
FIG. 4 is a schematic control block diagram of an ultrasound imaging apparatus including a main body and an ultrasound probe, in accordance with an exemplary embodiment.
Figure 5:
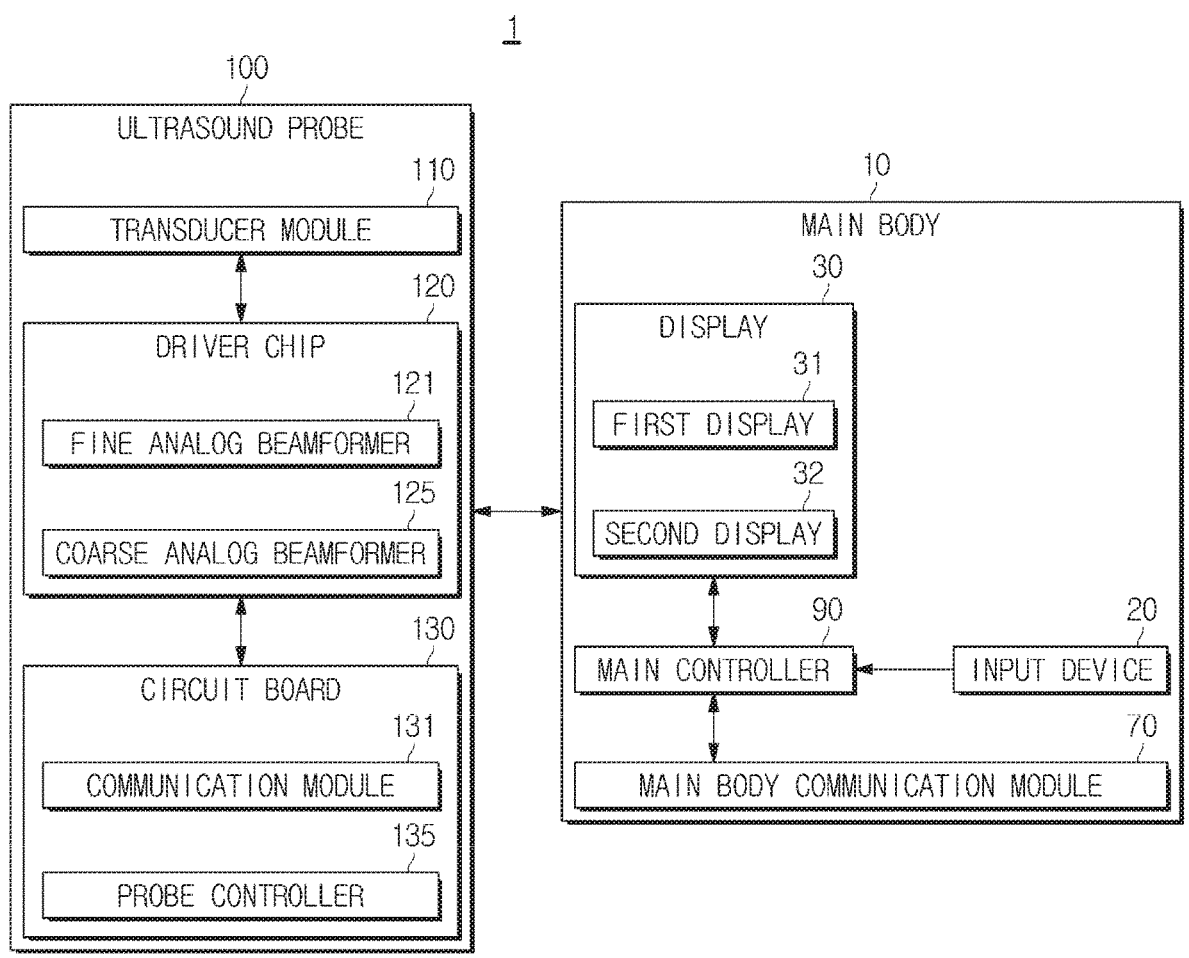
FIG. 5 is a schematic control block diagram of an ultrasound imaging apparatus including a main body and an ultrasound probe, in accordance with an exemplary embodiment different from that of FIG. 4.
Figure 6:
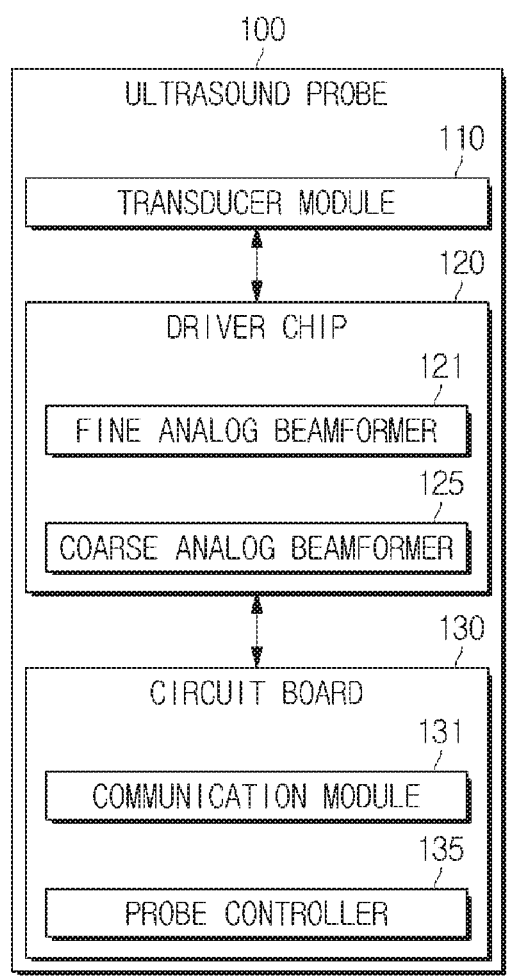
FIG. 6 is a schematic control block diagram of an ultrasound probe in accordance with an exemplary embodiment.
Figure 7A:
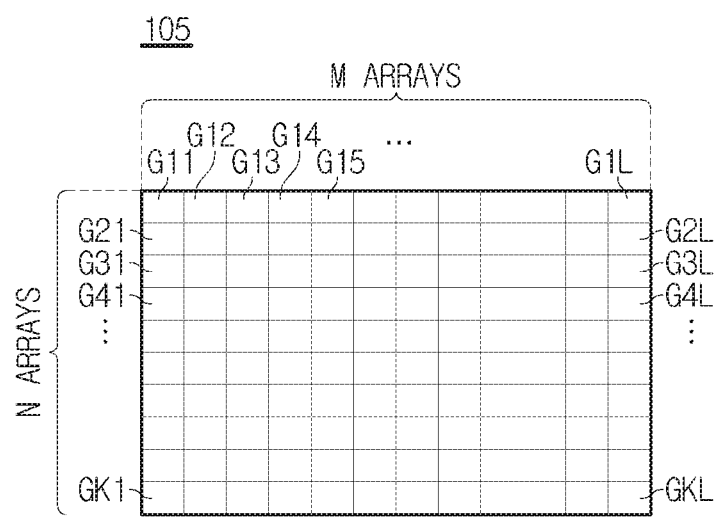
FIG. 7A is a diagram illustrating a plurality of subgroups of a 2D transducer array in accordance with an exemplary embodiment.
Figure 7B:
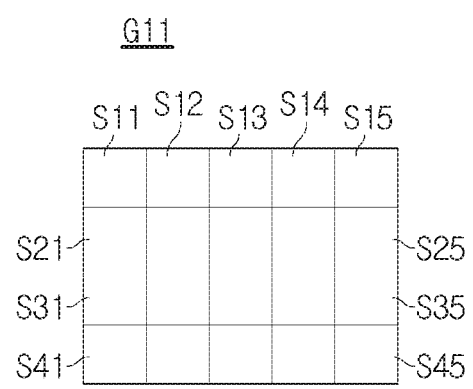
FIG. 7B is a diagram illustrating a transducer element included in one of a plurality of subgroups in accordance with an exemplary embodiment.
Figure 8:
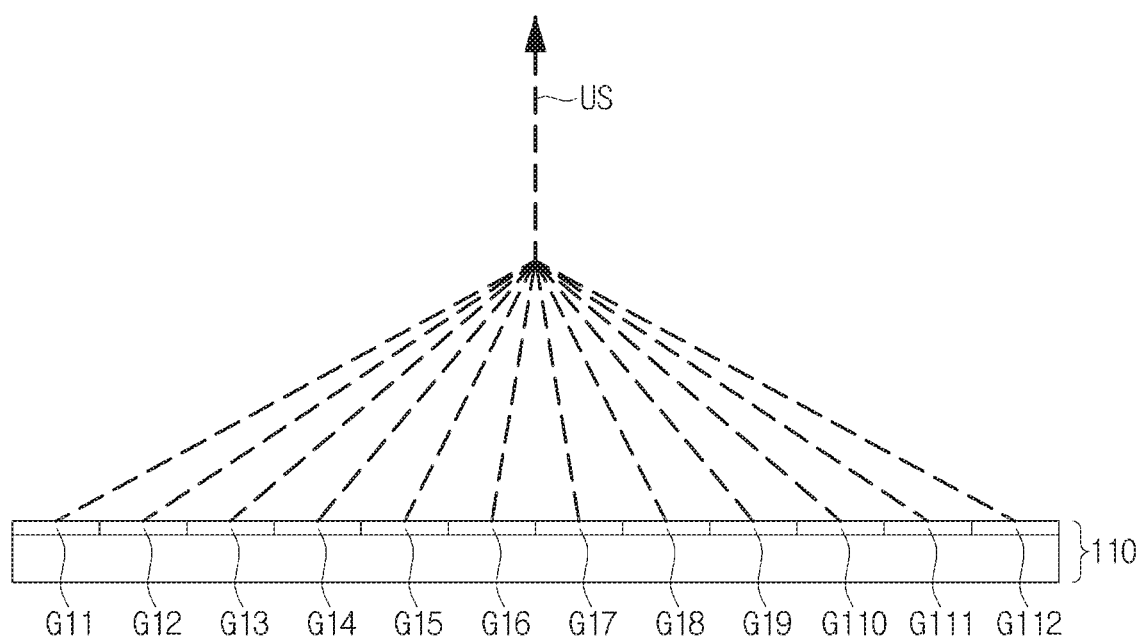
FIG. 8 is a diagram illustrating a case in which an ultrasound signal is transmitted by beamforming signals generated by a plurality of subgroups, in accordance with an exemplary embodiment.
Figure 9:
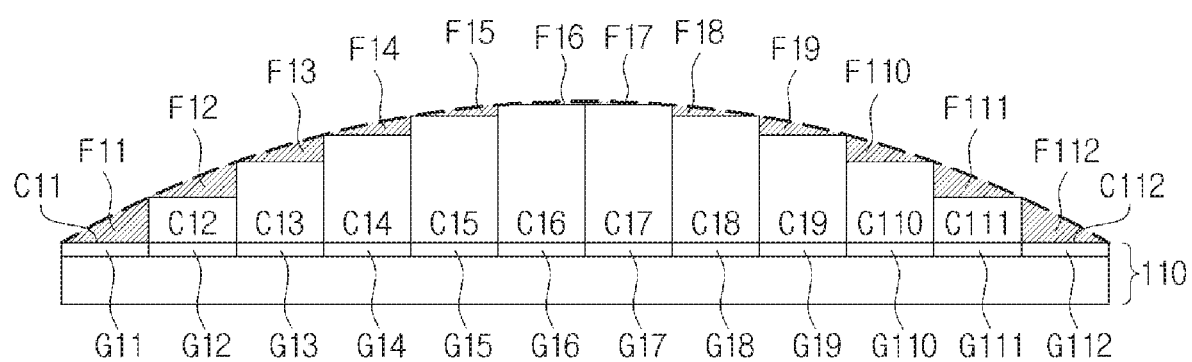
FIG. 9 is a diagram for explaining a fine delay and a coarse delay applied to beamform an ultrasound signal in accordance with an exemplary embodiment.

FIG. 4 is a schematic control block diagram of a main body and an ultrasound probe of an ultrasound imaging apparatus in accordance with an exemplary embodiment. FIG. 5 is a schematic control block diagram of a main body and an ultrasound probe of an ultrasound imaging apparatus in accordance with an exemplary embodiment different from that of FIG. 4. FIG. 6 is a schematic control block diagram of an ultrasound probe in accordance with an exemplary embodiment. FIG. 7A is a diagram illustrating a plurality of subgroups of a 2D transducer array in accordance with an exemplary embodiment. FIG. 7B is a diagram illustrating a transducer element included in one of a plurality of subgroups in accordance with an exemplary embodiment. FIG. 8 is a diagram illustrating a case in which an ultrasound signal is transmitted by beamforming signals generated by a plurality of subgroups, in accordance with an exemplary embodiment. FIG. 9 is a diagram for explaining a fine delay and a coarse delay applied to beamform an ultrasound signal in accordance with an exemplary embodiment.

Figure 10:
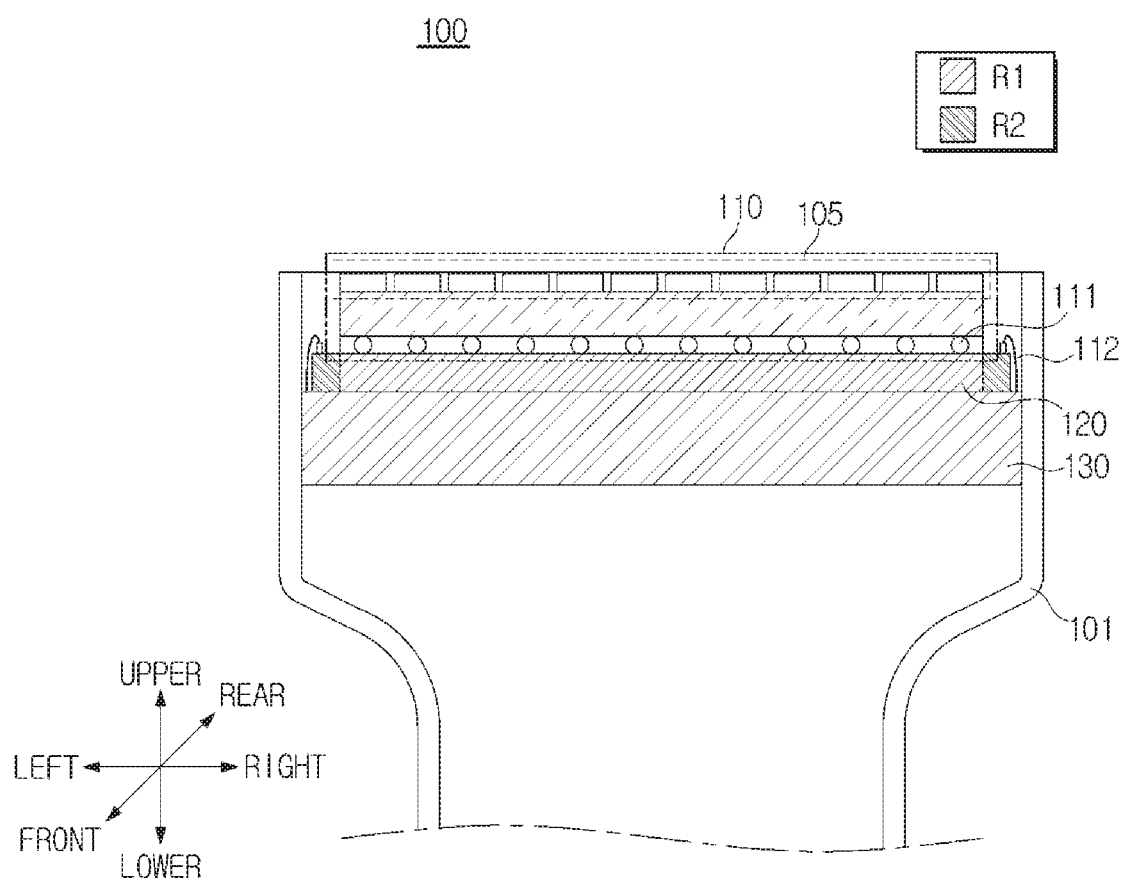
FIG. 10 is a schematic cross-sectional view of an ultrasound probe in accordance with an exemplary embodiment.
Figure 11:
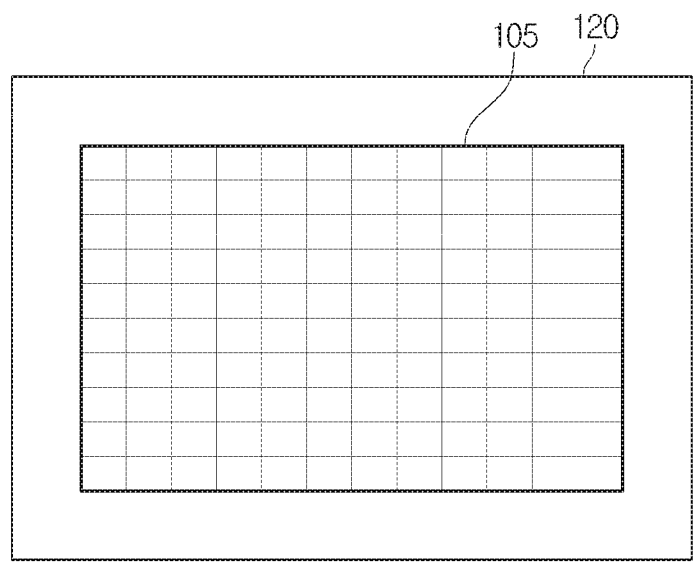
FIG. 11 is a top view of a transducer array and a driver chip in accordance with an exemplary embodiment.
Figure 12:
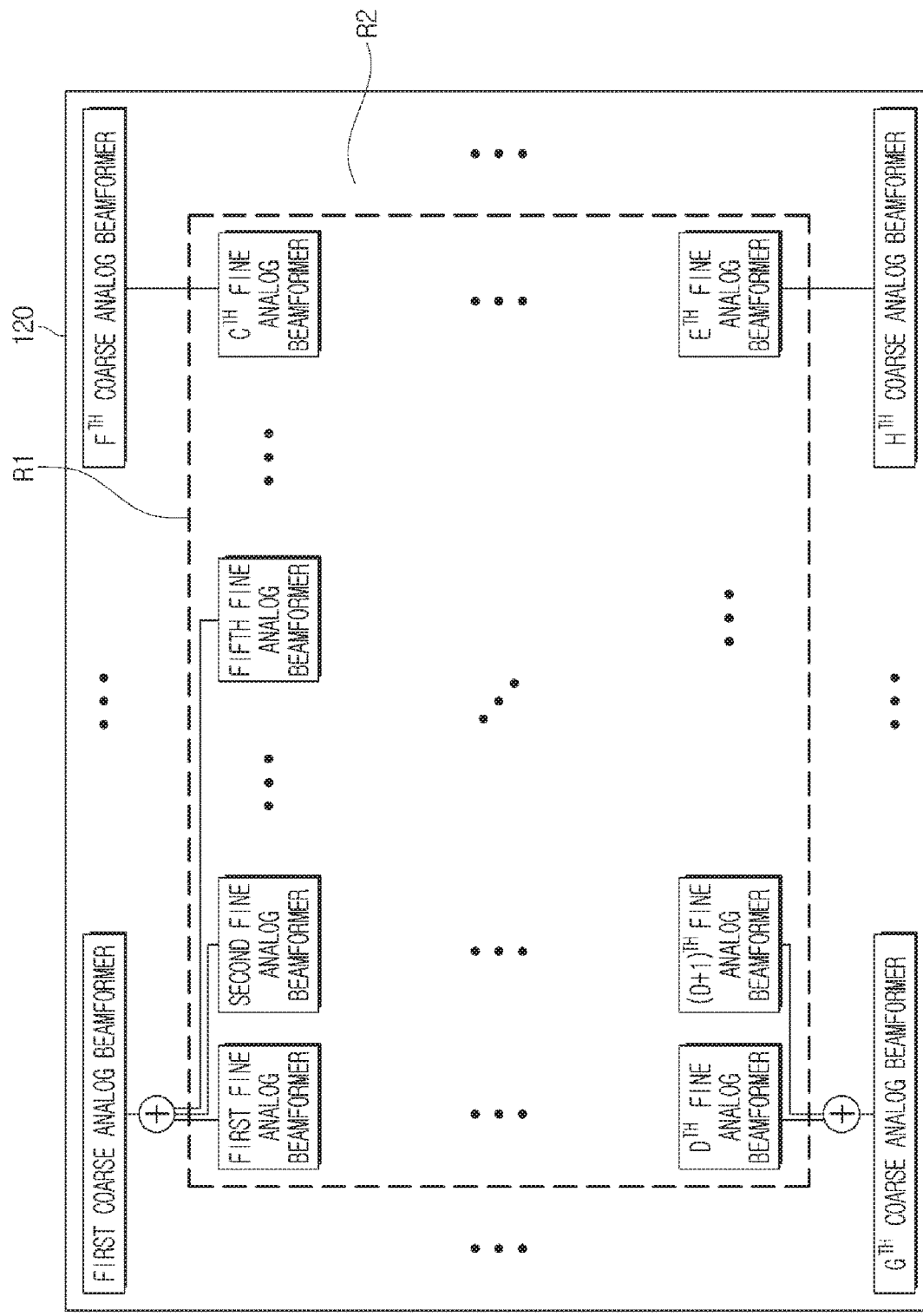
FIG. 12 is a diagram illustrating a fine analog beamformer and a coarse analog beamformer arranged in an inner region of the driver chip of FIG. 11.
Figure 13:
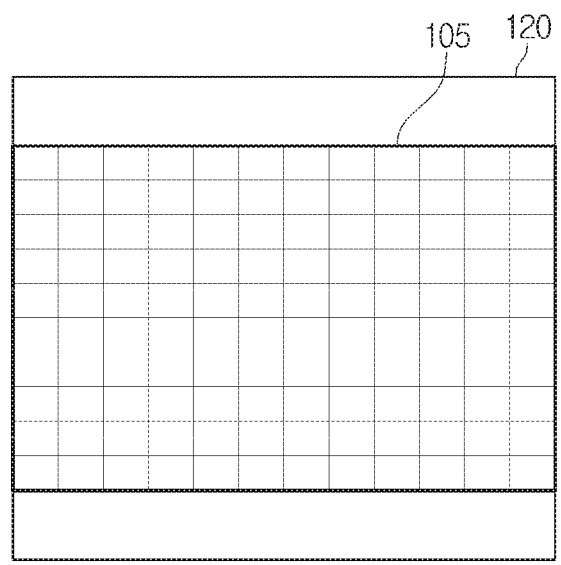
FIG. 13 is a top view of a transducer array and a driver chip, in accordance with another exemplary embodiment.
Figure 14:
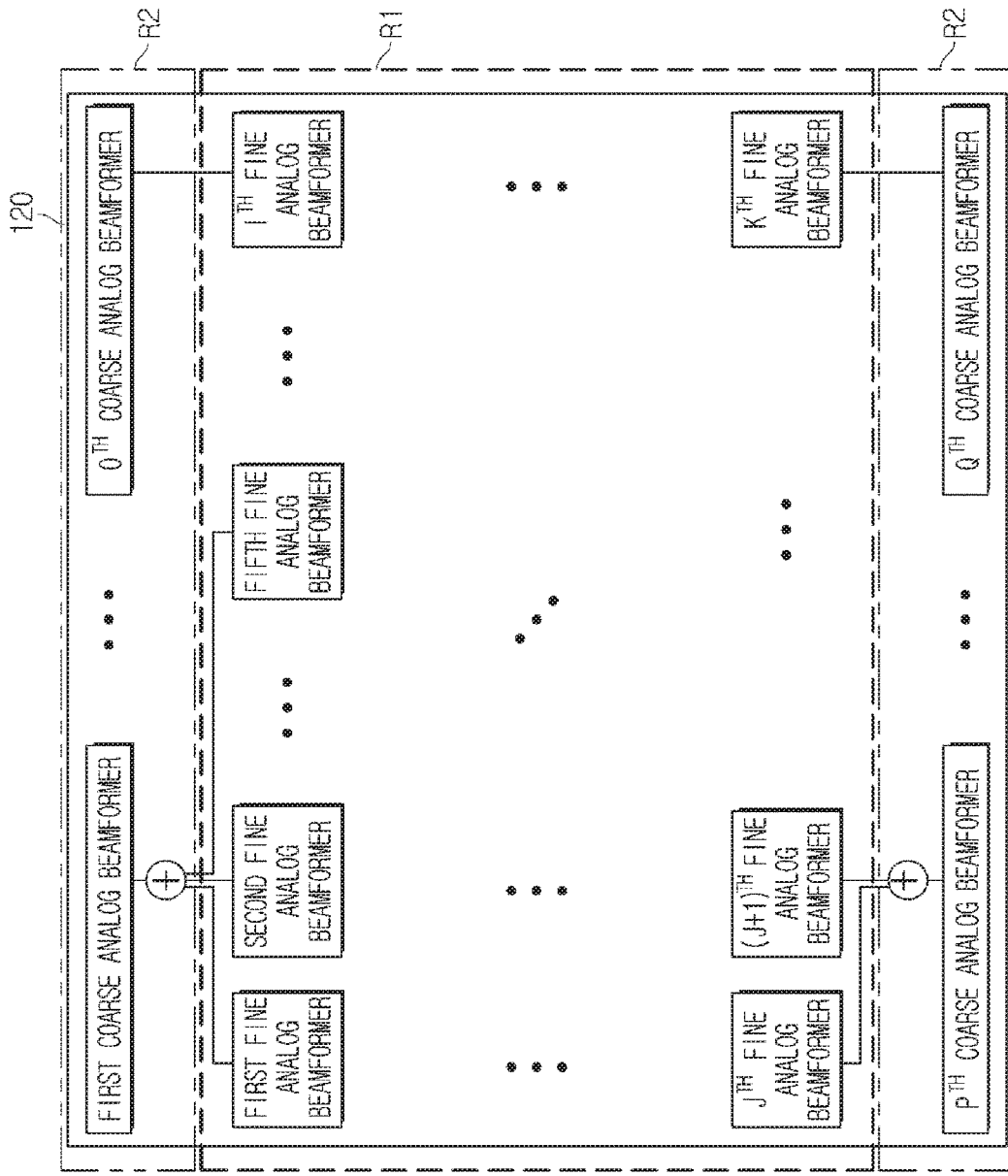
FIG. 14 is a diagram illustrating a fine analog beamformer and a coarse analog beamformer arranged in an inner region of the driver chip of FIG. 13.
Figure 15:
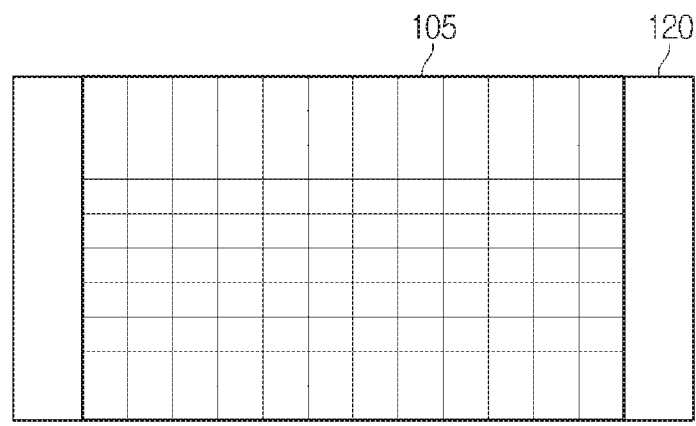
FIG. 15 is a top view of a transducer array and a driver chip in accordance with another exemplary embodiment.
Figure 16:
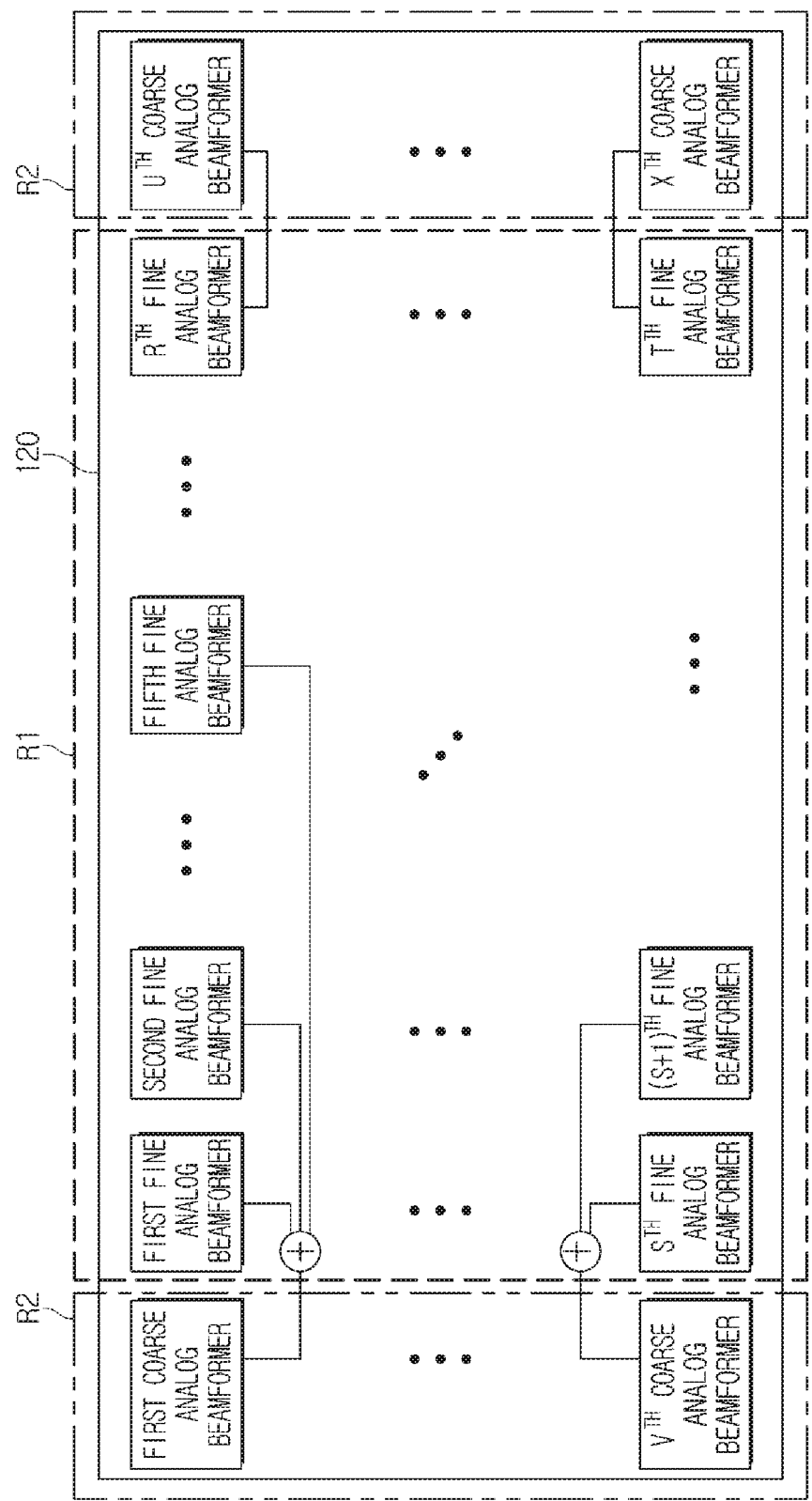
FIG. 16 is a diagram illustrating a fine analog beamformer and a coarse analog beamformer arranged in an inner region of the driver chip of FIG. 15.

FIG. 10 is a schematic cross-sectional view of an ultrasound probe in accordance with an exemplary embodiment. FIG. 11 is a top view of a transducer array and a driver chip in accordance with an exemplary embodiment. FIG. 12 is a diagram illustrating a fine analog beamformer and a coarse analog beamformer arranged in an inner region of the driver chip of FIG. 11. FIG. 13 is a top view of a transducer array and a driver chip, in accordance with another exemplary embodiment. FIG. 14 is a diagram illustrating a fine analog beamformer and a coarse analog beamformer arranged in an inner region of the driver chip of FIG. 13. FIG. 15 is a top view of a transducer array and a driver chip in accordance with another exemplary embodiment. FIG. 16 is a diagram illustrating a fine analog beamformer and a coarse analog beamformer arranged in an inner region of the driver chip of FIG. 15. FIGS. 4 to 16 will be described together below to avoid redundancy.

Referring to FIGS. 4 and 5, an ultrasound imaging apparatus 1 may include an ultrasound probe 100 and a main body 10 as described above. In this case, the ultrasound probe 100 and the main body 10 may be connected to each other through a connection member 40 via a wired communication network to exchange various types of data as described above. Alternatively, the main body 10 may include a main body communication module 70 configured to support wireless communication and thus the ultrasound probe 100 and the main body 10 may be connected to each other via a wireless communication network to exchange various types of data as illustrated in FIG. 5. In other words, the ultrasound probe 100 and the main body 10 may be connected via various types of communication networks to exchange various types of data but exemplary embodiments are not limited thereto.

The ultrasound probe 100 which is one of the components of the ultrasound imaging apparatus 1 will be described in more detail below.

Referring to FIG. 6, the ultrasound probe 100 may include a transducer module 110 configured to transmit an ultrasound signal to a subject and receive an echo ultrasound signal, a driver chip 120 electrically connected to the transducer module 110 and configured to focus ultrasound signals or echo ultrasound signals, and a circuit board 130 including a communication module 131 configured to exchange various types of data with the ultrasound imaging apparatus 1 or an external device and a probe controller 135 configured to control the overall operation of the ultrasound probe 100.

The transducer module 110 may include a transducer array 105. In this case, the transducer module 110 may transmit an ultrasound signal via the transducer array 105 which is a 2D M×N matrix type transducer array as illustrated in FIG. 7A, in which for example, M, N≥1. Furthermore, the transducer module 110 may receive an echo ultrasound signal reflected from a subject via the transducer array 105.

For example, the transducer array 105 may include 60×40 matrix type transducer elements. In this case, the transducer array 105 may include 2400 transducer elements.

The transducer array 105 of the transducer module 110 may include a plurality of subgroups. Here, the term "subgroup" may be also referred to as a subarray but the term "subgroup" will be used herein for convenience of explanation.

In one exemplary embodiment, the transducer array may be divided into a plurality of subgroups G11, G12, . . . , G1L, G21, G22, . . . , G2L, GK1, GK2, . . . , GKL: G as illustrated in FIG. 7A, in which, for example, K, L≥2.

Each of the subgroups G may include transducer elements forming an A×B matrix. As an example, in the present exemplary embodiment, A, B≥1. In one exemplary embodiment, referring to FIGS. 7A and 7B, one subgroup G11 may include transducer elements S11, S12 . . . S15, S21, S22, . . . , S25, S31, S32, . . . , S35, S41, S42, . . . , S45: S which form a 5×4 matrix. In this case, each of the transducer elements S belonging to a subgroup G may include various transmitting/receiving circuits for generating an ultrasound signal and receiving an echo ultrasound signal.

The number of subgroups may be predetermined according to ultrasound image channel information and the number of transducer elements of the transducer array 105.

For example, the transducer module 110 may include a transducer array including 2400 transducer elements arranged in a 60×40 matrix. In this case, in order to generate a 120-channel ultrasound image, a transducer array may include 200 subgroups, each consisting of a 5×4 matrix. In other words, as a channel of an ultrasound image increases, i.e. as a resolution of the ultrasound image increases, the number of subgroups G may increase.

Furthermore, each of the transducer elements S belonging to each subgroup G may include a transmitting/receiving circuit for beamforming an ultrasound signal or an echo ultrasound signal.

For example, the transmitting/receiving circuit may include a pulser configured to apply a pulse to transmit an ultrasound signal, a fine analog beamformer designed in an analog manner to apply a fine delay, etc. The transmitting/receiving circuit may further include a pad for connecting the driver chip 120 and the transducer module 110 which will be described below, and the like. In addition, the transmitting/receiving circuit may include various elements to generate and transmit an ultrasound signal and to receive an echo ultrasound signal but exemplary embodiments are not limited thereto.

For example, when a transducer array is a 60×40 matrix array, the transducer array may include 2400 transducer elements and ultrasound signals transmitted via the transducer array may have 2400 channels accordingly. In one exemplary embodiment, the driver chip 120 of the ultrasound probe 100 may have a built-in fine analog beamformer 121 and coarse analog beamformer 125 and thus may focus and transmit ultrasound signals.

Each of the echo ultrasound signals corresponding to the ultrasound signals may be received via one of the transducer elements of the transducer array. For example, the echo ultrasound signals may have 2400 channels. In this case, a desired-channel ultrasound image may be obtained when the echo ultrasound signals are focused.

In one exemplary embodiment, the ultrasound probe 100 may include the fine analog beamformer 121 and the coarse analog beamformer 125, which may be a coarse delay analog beamformer in exemplary embodiments, which are designed in an analog manner to focus echo ultrasound signals or ultrasound signals, i.e., to beamform the echo ultrasound signals or the ultrasound signals.

Generally, in order to obtain an ultrasound image, a transducer array of an ultrasound probe should be in contact with a surface of a subject. In this case, when the amount of heat generated in the ultrasound probe is high, there is a risk of the subject being burned. Accordingly, regulations regarding the amount of heat to be generated in the ultrasound probe, a power consumption rate of the ultrasound probe, etc. have been made. For example, there are regulations that a power consumption rate of an ultrasound probe should be in a range of about 2.5 W to less than 3.5 W and a temperature of a transducer array should be 43 degrees or less.

Conventionally, a digital beamformer designed as a digital logic to apply a coarse delay is provided in a main body of an ultrasound imaging apparatus. The above-described regulations should be complied with so that the digital beamformer may be included in the ultrasound probe. In this case, a digital beamformer may consume power of about 80 mW to control the coarse delay.

In one exemplary embodiment, 128 digital beamformers are required to output 128-channel echo signals and thus a power consumption rate of the 128 digital beamformers does not meet the above-described regulations. Furthermore, an analog-digital converter (ADC) which converts an analog signal into a digital signal is additionally required to use the digital beamformers. Accordingly, the above-described regulations cannot be complied with.

In one exemplary embodiment, the ultrasound probe 100 may include a single integrated circuit manufactured by designing a beamformer in an analog manner to apply a coarse delay. Accordingly, the ultrasound probe 100 may apply not only a fine delay but also a coarse delay to beamform an ultrasound signal or an echo ultrasound signal, thereby decreasing the amount of calculations required in the main body 10. Thus, the main body 10 of the ultrasound imaging apparatus 1 in accordance with an exemplary embodiment may be embodied as a small-sized terminal such as a smart phone, a mobile terminal, or a wearable terminal as described above.

When beamformers configured to apply a coarse delay are designed in an analog manner, problems caused by a large amount of heat generated may be solved. In this case, in order to design a fine analog beamformer and a coarse analog beamformer in an analog manner, various types of physical elements, e.g., a switched-capacitor, should be included in the units of subgroups. Thus, it is difficult for the fine analog beamformer and the coarse analog beamformer to be manufactured in a single chip.

In one exemplary embodiment, a fine analog beamformer may be designed to be provided in an inner region of the driver chip 120 of the ultrasound probe 100 corresponding to or facing a transducer array, and a coarse analog beamformer coupled to an output terminal of the fine analog beamformer may be designed to be provided in the other region of the driver chip 120. Accordingly, the driver chip 120 of the ultrasound probe 100 in accordance with an exemplary embodiment is designed as a single chip, in which the coarse analog beamformer embodied in an analog manner is provided in a region, i.e., an empty region, of the driver chip 120 except a region thereof in which the fine analog beamformer is provided, thereby minimizing the size of the ultrasound probe 100, as will be described in detail below.

A coarse delay which will be described below refers to a delay applied to compensate for the differences between positions of subgroups. For example, in order to generate an ultrasound signal by focusing ultrasound signals generated by the subgroups at a specific point, e.g., a focus point, a delay should be applied to the ultrasound signal generated by each of the subgroups in consideration of the differences between the positions of the subgroups. A device configured to apply a coarse delay will be referred to as a coarse analog beamformer.

Referring to FIG. 8, the ultrasound probe 100 may transmit an ultrasound signal US obtained by focusing sub-ultrasound signals generated by the first to twelfth subgroups G11, G12, . . . , G112. In this case, there are the differences between the positions of the first to twelfth subgroups G11, G12, . . . , G112 with respect to the focus point and thus a delay should be applied thereto.

When echo ultrasound signals are received by the subgroup, the echo ultrasound signals are received at different times due to the differences between the positions of the subgroups. Thus, a delay should be applied to the received echo ultrasound signals in consideration of the differences between the positions of the subgroups.

Similarly, there are the differences between positions of a plurality of transducer elements belonging to each subgroup. Thus, a focusing rate of ultrasound signals may be increased and a clearer ultrasound image may be obtained by compensating for the differences between the positions of the plurality of transducer elements belonging to each subgroup. In this case, a delay applied to compensate for the differences between the positions of the plurality of transducer elements belonging to each subgroup is referred to as a fine delay, and a device configured to apply the fine delay is referred to as a fine analog beamformer. The sum of a coarse delay and a fine delay applied to each of the plurality of transducer elements corresponds to a total delay value applied to each of the plurality of transducer elements.

For example, coarse delay values C11, C12, . . . , C112 and fine delay values F11, F12, . . . , F112 of the first to twelfth subgroups G11, G12, . . . , G112 may be illustrated as in FIG. 9. Referring to FIG. 9, in the first to twelfth subgroups G11, G12, . . . , G112, it can be confirmed that the coarse delay values C11, C12, . . . , C112 are constant and the fine delay values F11, F12, . . . , F112 vary. That is, the same coarse delay values are provided to transducer elements belonging to the same subgroup but different fine delay values may be applied thereto.

However, FIG. 9 illustrates that a focus point is a midpoint among the first to twelfth subgroups G11, G12, . . . , G112 and a coarse delay value of each of these subgroups and a fine delay value of transducer elements belonging to each of these subgroups may vary according to a position of a focus point.

Generally, in order to realize a fine analog beamformer and a coarse analog beamformer in an analog manner, a physical element such as a switched-capacitor element is required and thus it is difficult to manufacture an ultrasound probe in a small size. Thus, the fine analog beamformer or the coarse analog beamformer may be provided in a main body of an ultrasound imaging apparatus. Generally, a beamformer for applying a coarse delay is embodied as a digital logic and provided in a main body of an ultrasound imaging apparatus.

In this case, the ultrasound probe 100 in accordance with an exemplary embodiment may include a single chip having an appropriate arrangement of a fine analog beamformer and a coarse analog beamformer and thus may be manufactured in a small size. Furthermore, the main body 10 of the ultrasound imaging apparatus 1 does not include a beamformer for applying a coarse delay and thus a manufacturing cost of the main body 10 may be decreased. In addition, the amount of calculations of the main body 10 decreases and thus a small-sized terminal such as a smart phone, a mobile terminal, or a wearable terminal is applicable as the main body 10. The driver chip 120 having the fine analog beamformer 121 and the coarse analog beamformer 125 will be described in more detail below.

Referring to FIG. 10, the ultrasound probe 100 may include a case 101, and the transducer module 110 including transducer array 105 provided at a side of the case 101.

The driver chip 120 may be provided at a part of the transducer module 110. For example, as illustrated in FIG. 10, the driver chip 120 may be provided at a bottom of the transducer module 110, and electrically connected to the transducer module 110 via a pad 111 to control driving of the transducer module 110. For example, the driver chip 120 may control driving of the transducer elements of the transducer module 110 and apply a delay. Alternatively, the transducer module 110 and the driver chip 120 may be connected to each other via an interposer rather than the pad 111.

Furthermore, the circuit board 130 may be provided at a part of the driver chip 120. For example, the circuit board 130 may be provided at the bottom of the driver chip 120 as illustrated in FIG. 10. The driver chip 120 may be electrically connected to the circuit board 130 via a wire 112.

The driver chip 120 may have a larger area than that of the transducer array 105.

The driver chip 120 may include the fine analog beamformer 121 and the coarse analog beamformer 125 as described above.

In this case, in order to obtain a single driver chip 120, the driver chip 120 may be previously designed such that the fine analog beamformer 121 and the coarse analog beamformer 125 are efficiently arranged in an inner region thereof.

Inner regions of the driver chip 120 in which the fine analog beamformer 121 and the coarse analog beamformer 125 are respectively arranged may be previously set.

The inside of the driver chip 120 may be divided into a first region R1 and a second region R2. The first region R1 is a region facing or corresponding to the transducer module 110 and thus may be referred to as a core region. The second region R2 may correspond to an inner region of the driver chip 120, excluding the first region.

In the driver chip 120, the first region R1 and the second region R2 may be embodied in various forms.

For example, FIG. 11 is a top view of a transducer array 105 and a driver chip 120. The driver chip 120 may be provided to surround the transducer array 105 as illustrated in FIG. 11.

In this case, the inside of the driver chip 120 may be divided into a first region R1 and a second region R2 as illustrated in FIG. 12. The first region R1 is a region corresponding to the transducer array 105, in which first, ..., $c^{th}$, ..., $d^{th}$, ..., $e^{th}$ fine analog beamformers may be arranged to correspond to the transducer elements. As an example, in the present exemplary embodiment, $e \leq d \leq c > 1$. In the second region R2, first, ..., $f^{th}$, ..., $g^{th}$, ..., $h^{th}$ coarse analog beamformers may be arranged to correspond to subgroups. As an example, in the present exemplary embodiment, $h \geq g \geq f < 1$.

Signals output from a plurality of fine analog beamformers belonging to the same subgroup may be summed and input to one coarse analog beamformer via a connection terminal. For example, when 20 transducer elements belong to one subgroup as illustrated in FIG. 7B, signals output from first to twentieth fine analog beamformers may be summed and input to the first coarse analog beamformer via a connection terminal. In one exemplary embodiment, referring to FIG. 12, signals output from first to fifth fine analog beamformers may be summed and input to the first coarse analog beamformer.

The sizes and arrangement of the transducer array 105 and the driver chip 120 are not limited to those described above.

FIG. 13 is a top view of a transducer array 105 and a driver chip 120. A horizontal length of the driver chip 120 may be equal to that of the transducer array 105 but a vertical length thereof may be greater than that of the transducer array 105 as illustrated in FIG. 13. In this case, the inside of the driver chip 120 may be divided into a first region R1 and a second region R2 as illustrated in FIG. 14. In the first region R1, first, ..., ith, ..., jth, ..., kth fine analog beamformers may be arranged to correspond to transducer elements. As an example, in the present exemplary embodiment, $k \geq j \geq i > 1$. In the second region R2, first, ..., $o^{th}$, ..., $p^{th}$, ..., $q^{th}$ coarse analog beamformers may be arranged to correspond to subgroups. As an example, in the present exemplary embodiment, $q \geq p \geq o > 1$.

FIG. 15 is a top view of a transducer array 105 and a driver chip 120. A vertical length of the driver chip 120 may be equal to that of the transducer array 105 but a horizontal length thereof may be different from that of the transducer array 105 as illustrated in FIG. 15.

In this case, the inside of the driver chip 120 may be divided into a first region R1 and a second region R2 as illustrated in FIG. 16. In the first region R1, first, ..., $r^{th}$, ..., $s^{th}$, ... $t^{th}$ fine analog beamformers may be arranged to correspond to transducer elements. As an example, in the present exemplary embodiment, $t \geq s \geq r > 1$. In the second region R2, first, ..., $u^{th}$, ..., $v^{th}$, ..., $x^{th}$ coarse fine analog beamformers may be arranged to correspond to subgroups. As an example, in the present exemplary embodiment, $x \geq v \geq u > 1$.

In another exemplary embodiment, the driver chip 120 is a single chip which is capable of performing 2-stage analog beamforming, reducing the amount of calculations of the main body 10, and minimizing the size of the ultrasound probe 100. For example, the driver chip 120 may be embodied as an application specific integrated circuit (ASIC) designed and manufactured in consideration of the sizes and arrangement of the transducer array 105 and the driver chip 120.

In this case, a signal flow between the fine analog beamformer 121 and the coarse analog beamformer 125 via a connection terminal may be different according to whether an ultrasound signal is transmitted or whether an echo ultrasound signal is transmitted.

For example, when ultrasound signals are transmitted, the probe controller 135 of the circuit board 130 which will be described below may control the coarse analog beamformer 125 using a control signal to set a coarse delay per subgroup. Next, the probe controller 135 of the circuit board 130 may control the fine analog beamformer 121 using a control signal to set a fine delay for each of transducer the elements belonging to each subgroup. Thus, the transducer module 110 may transmit an ultrasound signal beamformed according to the set delays.

As another example, when echo ultrasound signals are received, the probe controller 135 of the circuit board 130 controls the fine analog beamformer 121 using a control signal to set a fine delay for each of the transducer elements. Then, the echo ultrasound signals to which a fine delay is applied via the fine analog beamformer 121 may be summed per subgroup and then input to the coarse analog beamformer 125. The coarse analog beamformer 125 may apply a coarse delay to a signal input thereto and output a resultant signal. For convenience of explanation, the output signal described above will be referred to as an echo signal.

The echo signal may be transmitted to the circuit board 130 via the wire 112. The probe controller 135 of the circuit board 130 may transmit the echo signal to the main body 10, transmit an ultrasound image reconstructed through an image processing process, or perform various other operations. The circuit board 130 of the ultrasound probe 100 will be described below.

The circuit board 130 may be provided at a bottom of the driver chip 120 as illustrated in FIG. 10. The circuit board 130 may be manufactured to have the same size as or to be smaller or larger than the driver chip 120 but is not limited thereto. Here, the circuit board 130 may be embodied as a printed circuit board (PCB) or a flexible printed circuit board (FPCB).

The circuit board 130 may include the communication module 131 configured to transmit a signal or data to or receive a signal or data from the main body 10 or an external device via a communication network, and the probe controller 135 configured to control the overall operation of the ultrasound probe 100.

The probe controller 135 may be embodied as hardware or may be embodied as software executable by hardware but is not limited thereto. For example, the probe controller 135 may be embodied as a processor, such as a micro-control unit (MCU), which is capable of performing various types of image processing, various operations, etc. but is not limited thereto.

When the probe controller 135 is embodied as hardware, the probe controller 135 and the communication module 131 may be embodied as different elements and included in the circuit board 130 or may be integrated together on one system-on-chip (SoC) and included in the circuit board 130 but are not limited thereto.

The communication module 131 may include at least one component configured to establish communication with an external device. For example, the communication module 131 may include at least one among a short-range communication module supporting a short-range communication method, a wired communication module supporting a wired communication method, and a wireless communication module supporting a wireless communication method. The short-range communication module, the wired communication module, and the wireless communication module are as described above in detail and thus are not described again here.

The communication module 131 may transmit various signals or data to the main body 10 via a communication network. For example, the communication module 131 may transmit an echo signal to the main body 10 via the communication network or transmit an ultrasound image reconstructed through an image processing process to the main body 10. Alternatively, the communication module 131 may transmit data on which only some image processing processes are performed to the main body 10. In this case, the echo signal, the ultrasound image, or the data on which only some image processing processes are performed may be transmitted to the main body 10 according to an operation of the probe controller 135.

Furthermore, the communication module 131 may receive various types of commands from the main body 10 via the communication network but is not limited thereto. For example, the communication module 131 may receive various types of control commands, which are input by a user through the input device 20, from the main body 10 via the communication network. The probe controller 135 may control operations of the components of the ultrasound probe 100 according to a control command. The probe controller 135 will be described below.

The probe controller 135 may generate a control signal and control the components of the ultrasound probe 100 using the generated control signal. For example, the circuit board 130 may include a memory storing a control program, control data, etc. to be used to control the ultrasound probe 100. The probe controller 135 may control the components of the ultrasound probe 100 by generating a control signal using the data stored in the memory.

In one exemplary embodiment, the probe controller 135 may control the transducer module 110 and the driver chip 120 to transmit an ultrasound signal using the control signal. In another exemplary embodiment, the probe controller 135 may control the driver chip 120 to apply a delay to an echo ultrasound signal received via the transducer module 110, and output an echo signal corresponding to a desired channel. The probe controller 135 may control the communication module 131 to transmit an output echo signal to the main body 10. Alternatively, the probe controller 135 may generate an ultrasound image by performing an image processing process on an output echo signal, and control the communication module 131 to transmit the ultrasound image to the main body 10. Alternatively, the probe controller 135 may obtain data by performing only some image processing processes, which are required to generate an ultrasound image, on an output echo signal, and control the communication module 131 to transmit this data to the main body 10.

In some cases, the ultrasound probe 100 may further include a power module configured to supply power, a display, an input device, etc.

The power module may supply power to the ultrasound probe 100. In detail, the power module converts electric energy into chemical energy, accumulates the chemical energy, and supplies power by converting the accumulated chemical energy into electric energy. In one exemplary embodiment, the power module may be embodied as a lithium ion battery, a nickel hydride battery, a polymer battery, or the like. However, the power module is not limited thereto and may be embodied as various types of batteries which may be included in the ultrasound probe 100 and configured to supply power.

The power module may be charged by being directly connected to a charging device according to a wired charging method or may be charged according to a wireless charging method. That is, the power module may be charged according to various well-known methods but is not limited thereto.

When the ultrasound probe 100 is connected to the main body 10 of the ultrasound imaging apparatus 1 according to a wired communication method, the power module may be included in the ultrasound probe 100 if necessary or may be omitted but is not limited thereto.

The ultrasound probe 100 may further include a display in some cases.

The display may display information related to an operating state of the ultrasound probe 100, e.g., a power state of the ultrasound probe 100.

In some cases, the ultrasound probe 100 may further include an input device. The input device may be embodied in the form of a switch, a key, or the like as described above but is not limited thereto. The input device may be configured to receive a command to power on the ultrasound probe 100, a command to power off the ultrasound probe 100, a control command to change an operating mode of the ultrasound probe 100 etc. from a user, but exemplary embodiments are not limited thereto. The main body 10 of the ultrasound imaging apparatus 1 will be described below.

The main body 10 of the ultrasound imaging apparatus 1 may include an input device 20, a display 30, a connection member 40, and a main controller 90 as illustrated in FIG. 4. Alternatively, in some cases, the main body 10 of the ultrasound imaging apparatus 1 may include an input device 20, a display 30, a main body communication module 70, and a main controller 90 as illustrated in FIG. 5. The input device 20, the display 30, and the connection member 40 are as described above in detail and thus are not described again here.

The main body communication module 70 may include at least one component configured to establish communication with an external device. For example, the main body communication module 70 may include at least one of a short-range communication module supporting a short-range communication method and a wireless communication module supporting a wireless communication method. The short-range communication module and wireless communication module are as described above in detail and thus are not described again here.

The main body communication module 70 may transmit a control signal to the ultrasound probe 100. For example, when a control command is received from a user via the input device 20, the main body communication module 70 may transmit a control signal to the ultrasound probe 100 and thus the ultrasound probe 100 may be operated according to the control command from the user.

In addition, the main body communication module 70 may exchange various types of data with the ultrasound probe 100. For example, the main body communication module 70 may receive at least one among an echo signal, an ultrasound image, and data obtained by performing some image processing processes from the ultrasound probe 100. The main controller 90 will be described below.

The main controller 90 may be embodied in the form of hardware, e.g., a processor or may be embodied in the form of software which is executable by hardware.

For example, the main controller 90 may be embodied as at least one of a processor capable of performing various processes such as an image processing process and an execution processing process and a graphics processor or may be embodied as a single component having functions of these processors.

The main controller 90 may generate a control signal and control overall operations of internal components of the main body 10 using the generated control signal. For example, the main body 10 may include a memory, in which control data for controlling the components of the ultrasound probe 100 and control data for performing an image processing process have been previously stored. The main controller 90 may generate a control signal on the basis of the data stored in the memory, and control overall operations of the components of the main body 10 using the generated control signal.

The main controller 90 may reconstruct an ultrasound image by performing an image processing process on an echo signal on the basis of the data stored in the memory. In one exemplary embodiment, the main controller 90 may generate an ultrasound image by performing a scan conversion process on the echo signal. Here, the ultrasound image may be understood to include a Doppler image representing a moving subject using the Doppler effect, as well as a gray-scale image obtained by scanning a subject in an amplitude mode (A mode), a brightness mode (B mode) and a motion mode (M mode). Examples of the Doppler image may include a blood flow Doppler image representing blood flow (which may be also referred to as a color Doppler image), a tissue Doppler image representing tissue movement, and a spectral Doppler image representing a moving speed of a subject as a waveform.

In order to generate a B-mode image, the main controller 90 may extract a B-mode component from an echo signal received by the ultrasound probe 100. The main controller 90 may generate an ultrasound image expressed such that the intensity of an echo ultrasound wave is warped on the basis of the B-mode component.

Likewise, the main controller 90 may extract a Doppler component from an echo signal, and generate a Doppler image representing a movement of a subject using colors or waveforms on the basis of the extracted Doppler component.

Furthermore, the main controller 90 may generate a three-dimensional (3D) ultrasound image by performing volume rendering on volume data obtained from an echo signal, or may generate an elastic image representing a degree of deformation of a subject due to pressure applied thereto. In addition, the main controller 90 may represent various types of additional information in an ultrasound image in the form of text or graphics.

The generated ultrasound image may be stored in a memory included in the main body 10 or in an external memory. However, exemplary embodiments are not limited thereto, and the ultrasound image may be stored in either a Web storage system performing a storage function on the Web or a cloud server via the main body communication module 70 of FIG. 5.

As described above, all operations related to an image processing process required to obtain an ultrasound image may be performed by the main controller 90. Alternatively, some or all the operations related to the image processing process required to obtain an ultrasound image may be performed by the probe controller 135 of the ultrasound probe 100.

The main controller 90 may control an ultrasound image of a subject to be displayed on the display 30 so that the subject may be diagnosed. A flow of operations of an ultrasound imaging apparatus to transmit an ultrasound signal and receive an echo ultrasound signal will be briefly described below.

Figure 17:
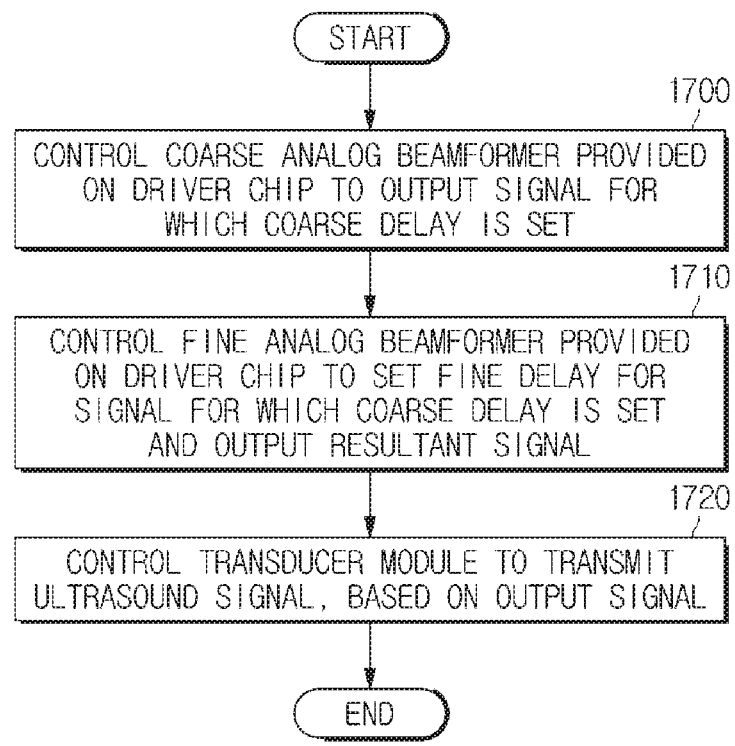
FIG. 17 is a schematic flowchart of an operation of an ultrasound imaging apparatus which transmits an ultrasound signal, in accordance with an exemplary embodiment.

FIG. 17 is a schematic flowchart of an operation of an ultrasound imaging apparatus which transmits an ultrasound signal, in accordance with one exemplary embodiment.

Referring to FIG. 17, an ultrasound imaging apparatus may control a coarse analog beamformer provided on a driver chip of an ultrasound probe to output a signal for which a coarse delay is set (1700). Here, the coarse delay is applied to compensate for the difference between positions of subgroups of a transducer array. As a subgroup becomes farther from a focus point, a coarse delay value for the subgroup may increase.

In the driver chip, the coarse analog beamformer may be connected to a fine analog beamformer via a connection terminal. Accordingly, a signal output from the coarse analog beamformer may be supplied to the fine delay beamformer.

The ultrasound imaging apparatus may control the fine analog beamformer to set a fine delay for the signal output from the coarse analog beamformer and to output the resultant signal (1710).

The fine delay is applied to compensate for the difference between positions of transducer elements belonging to each subgroup. The ultrasound imaging apparatus may control a transducer module to transmit a beamformed ultrasound signal on the basis of the signal output from the fine analog beamformer (1720). In one exemplary embodiment, the ultrasound imaging apparatus includes, in the form of a single chip, a component for beamforming an ultrasound signal and thus may be manufactured in a small size.

Figure 18:
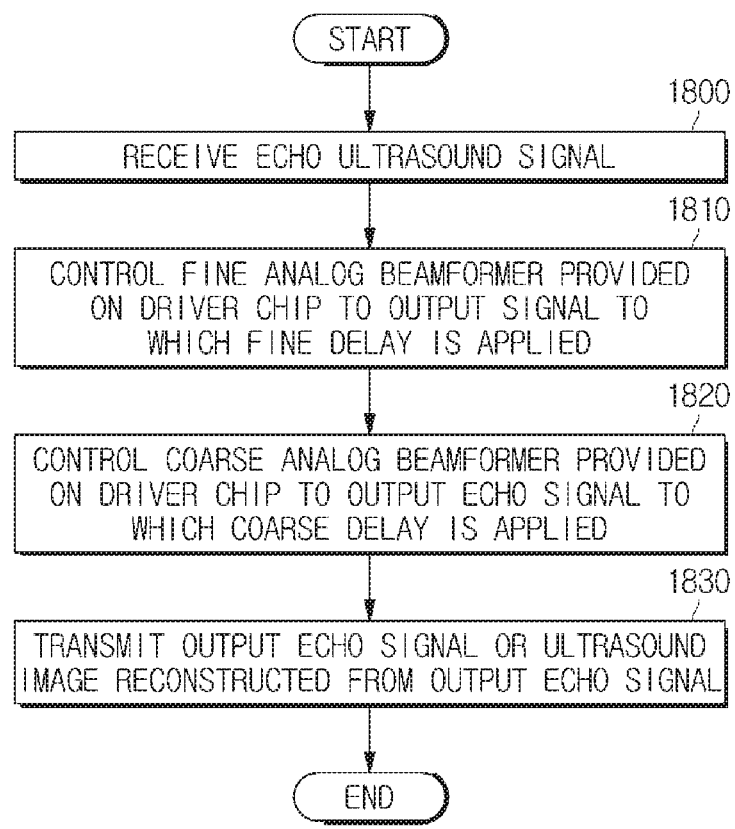
FIG. 18 is a schematic flowchart of an operation of an ultrasound imaging apparatus which receives an echo ultrasound signal and generates an ultrasound image, in accordance with an exemplary embodiment.

FIG. 18 is a schematic flowchart of an operation of an ultrasound imaging apparatus which receives an echo ultrasound signal and generates an ultrasound image, in accordance with one exemplary embodiment.

An ultrasound imaging apparatus may receive an echo ultrasound signal via a transducer module (1800). In this case, the ultrasound imaging apparatus may beamform the echo ultrasound signal to obtain a desired-channel ultrasound image.

For example, the ultrasound imaging apparatus may beamform an echo ultrasound signal through a single driver chip provided at a part of the transducer module. The ultrasound imaging apparatus may control a fine analog beamformer provided on the driver chip to output a signal obtained by applying a fine delay to the echo ultrasound signal (1810).

Each of echo ultrasound signals received by a plurality of transducer elements belonging to the same subgroup may be supplied to a fine analog beamformer of a transmitting/receiving circuit of one of the plurality of transducer element so as to apply a fine delay thereto.

Signals output from fine analog beamformers belonging to the same subgroup may be summed and input to a coarse analog beamformer. Then the ultrasound imaging apparatus may control the coarse analog beamformer to output an echo signal to which a coarse delay is applied (1820).

The ultrasound imaging apparatus may display an ultrasound image generated from the output echo signal (1830). The ultrasound imaging apparatus may generate an ultrasound image from an echo signal. In this case, the generation of the ultrasound image from the echo signal may be performed by an ultrasound probe or a main body of the ultrasound imaging apparatus. However, exemplary embodiments are not limited thereto and a process of generating an ultrasound image from an echo signal may be divided and performed by the ultrasound probe and the main body of the ultrasound imaging apparatus. The ultrasound imaging apparatus may display the ultrasound image on a display so that a subject may be diagnosed.

The exemplary embodiments set forth herein and the structures illustrated in the drawings are merely examples of the present disclosure. Various modified examples which may replace these exemplary embodiments and the drawings could have been made at the filing date of the present application.

The terminology used herein is for the purpose of describing particular exemplary embodiments only and is not intended to be limiting of the present disclosure. As used herein, the singular forms "a", "an" and "the" are intended to include the plural forms as well, unless the context clearly indicates otherwise. It will be understood that the terms "comprise" and/or "comprising," when used herein, specify the presence of stated features, integers, steps, operations, elements, components, or a combination thereof, but do not preclude the presence or addition of one or more other features, integers, steps, operations, elements, components, or a combination thereof.

It will be understood that, although the terms "first", "second", etc., may be used herein to describe various elements, the elements should not be limited by these terms. These terms are only used to distinguish one element from another element. For example, a first element could be termed a second element without departing from the scope of the present disclosure. Similarly, a second element could be termed a first element. As used herein, the term "and/or" includes any and all combinations of one or more of the associated listed items.

As used herein, the terms "unit", "device", "block", "member", "module", etc. may refer to a unit for processing at least one function or operation. For example, these terms may refer to software or hardware such as a field-programmable gate array (FPGA) or an ASIC. However, these terms are not limited to software or hardware and may refer to a structure stored in an accessible storage medium and executable by one or more processors.

Although a few exemplary embodiments of the present disclosure have been shown and described, it would be appreciated by those skilled in the art that changes may be made in these exemplary embodiments without departing from the principles and spirit of the disclosure, the scope of which is defined in the claims and their equivalents.

What is claimed is:

1. An ultrasound probe comprising:
    a transducer module configured to receive an echo ultrasound signal reflected from a subject in response to an ultrasound signal transmitted to the subject, and comprising a plurality of transducer elements divided into a plurality of subgroups; and
    a driver chip provided at the transducer module, the driver chip being configured to focus at least one of the ultrasound signal and the echo ultrasound signal,
    wherein the driver chip comprises:
    a fine analog beamformer configured to apply a fine delay, wherein the fine analog beamformer comprises a plurality of fine analog sub-beamformers; and
    a coarse analog beamformer configured to apply a coarse delay, wherein the coarse analog beamformer comprises a plurality of coarse analog sub-beamformers,
    wherein each fine analog sub-beamformer of the plurality of fine analog sub-beamformers is arranged to correspond to a respective transducer element of the plurality of transducer elements in a first inner region of the driver chip, the first inner region being located opposite to the transducer module, and
    wherein each coarse analog sub-beamformer of the plurality of coarse analog sub-beamformers is arranged to correspond to a respective subgroup of the plurality of subgroups in a second inner region of the driver chip, wherein the second inner region is a region excluding the first inner region from an inner region of the driver chip,
    wherein each coarse analog sub-beamformer of the plurality of coarse analog sub-beamformers is configured to receive as an input summed echo ultrasound signals output from a subset of the plurality of fine analog sub-beamformers and which are summed via a connection terminal.

2. The ultrasound probe according to claim 1, wherein the driver chip comprises an application-specific integrated circuit (ASIC).

3. The ultrasound probe according to claim 1, wherein a number of the plurality of subgroups is determined according to channel information of an ultrasound image and a number of transducer elements of the transducer module.

4. The ultrasound probe according to claim 1, further comprising a circuit board at a bottom of the driver chip, the circuit board including a probe controller configured to control the fine analog beamformer and the coarse analog beamformer.

5. The ultrasound probe according to claim 4, wherein the driver chip is electronically connected to the circuit board.

6. The ultrasound probe according to claim 4, wherein the probe controller is further configured to control the coarse analog beamformer to input a signal to which the coarse delay is applied to the fine analog beamformer, and to control the fine analog beamformer to transmit the ultrasound signal based on an output signal to which the fine delay is applied.

7. The ultrasound probe according to claim 4, wherein, when the echo ultrasound signal is received through the transducer module, the probe controller is further configured to control the fine analog beamformer to output a signal obtained by applying the fine delay to the echo ultrasound signal, and to control the coarse analog beamformer to output an echo signal by applying the coarse delay to an output signal.

8. An ultrasound imaging apparatus comprising:
an ultrasound probe comprising:
    a transducer module configured to receive an echo ultrasound signal reflected from a subject, in response to an ultrasound signal transmitted the subject, and comprising a plurality of transducer elements divided into a plurality of subgroups; and
    a driver chip provided at the transducer module, the driver chip being configured to focus at least one of the ultrasound signal and the echo ultrasound signal,
wherein the driver chip comprises:
    a fine analog beamformer configured to apply a fine delay, wherein the fine analog beamformer comprises a plurality of fine analog sub-beamformers; and
    a coarse analog beamformer configured to apply a coarse delay, wherein the coarse analog beamformer comprises a plurality of coarse analog sub-beamformers; and
    a main controller configured to control an ultrasound image generated based on the echo ultrasound signal to be displayed on a display,
wherein each fine analog sub-beamformer of the plurality of fine analog sub-beamformers is arranged to correspond to a respective transducer element of the plurality of transducer elements in a first inner region of the driver chip, the first inner region being located opposite to the transducer module, and
wherein each coarse analog sub-beamformer of the plurality of coarse analog sub-beamformers is arranged to correspond to a respective subgroup of the plurality of subgroups in a second inner region of the driver chip, wherein the second inner region is a region excluding the first inner region from an inner region of the driver chip,
wherein each coarse analog sub-beamformer of the plurality of coarse analog sub-beamformers is configured to receive as an input summed echo ultrasound signals output from a subset of the plurality of fine analog sub-beamformers and which are summed via a connection terminal.

9. The ultrasound imaging apparatus according to claim 8, wherein a number of the plurality of subgroups is determined according to channel information of the ultrasound image and a number of transducer elements of the transducer module.

10. The ultrasound imaging apparatus according to claim 8, further comprising a circuit board at a bottom of the driver chip, the circuit board including a probe controller configured to control the fine analog beamformer and the coarse analog beamformer.

11. The ultrasound imaging apparatus according to claim 10, wherein the probe controller is further configured to control the coarse analog beamformer to input a signal to which the coarse delay is applied to the fine analog beamformer, and to control the fine analog beamformer to transmit an ultrasound signal based on an output signal to which the fine delay is applied.

12. The ultrasound imaging apparatus according to claim 10, wherein, when the echo ultrasound signal is received through the transducer module, the probe controller is further configured to control the fine analog beamformer to output a signal obtained by applying the fine delay to the echo ultrasound signal, and to control the coarse analog beamformer to output an echo signal by applying the coarse delay to an output signal.

13. A method of controlling an ultrasound imaging apparatus, the method comprising:
    receiving an echo ultrasound signal in response to an ultrasound signal transmitted;
    outputting an echo signal by applying a fine delay and a coarse delay to the echo ultrasound signal using a fine analog beamformer and a coarse analog beamformer, wherein the fine analog beamformer comprises a plurality of fine analog sub-beamformers, and the coarse analog beamformer comprises a plurality of coarse analog sub-beamformers;
    displaying on a display an ultrasound image reconstructed based on the echo signal; and
    applying the coarse delay to a plurality of subgroups of a transducer array included in a transducer module by the plurality of coarse analog sub-beamformers,
wherein each fine analog sub-beamformer of the plurality of fine analog sub-beamformers is arranged to correspond to a respective transducer element of the plurality of transducer elements in a first inner region of a driver chip, the first inner region being located opposite to the transducer module, and
wherein each coarse analog sub-beamformer of the plurality of coarse analog sub-beamformers is arranged to correspond to a respective subgroup of the plurality of subgroups in a second inner region of the driver chip, wherein the second inner region is a region excluding the first inner region from an inner region of the driver chip,
wherein each coarse analog sub-beamformer of the plurality of coarse analog sub-beamformers is configured to receive as an input summed echo ultrasound signals output from a subset of the plurality of fine analog sub-beamformers and which are summed via a connection terminal.

\* \* \* \* \*